United States Patent
Cui et al.

(10) Patent No.: US 12,360,083 B1
(45) Date of Patent: Jul. 15, 2025

(54) METHOD AND SYSTEM FOR MEASURING BURNING RATE OF PROPELLANT BASED ON MULTI-CHANNEL ULTRASONIC WAVES

(71) Applicant: North University of China, Shanxi (CN)

(72) Inventors: Juan Cui, Shanxi (CN); Yongqiu Zheng, Shanxi (CN); Xiaolong Yan, Shanxi (CN); Wenlong Wei, Shanxi (CN); Ruizhi Wang, Shanxi (CN)

(73) Assignee: North University of China, Taiyuan (CN)

( * ) Notice: Subject to any disclaimer, the term of this patent is extended or adjusted under 35 U.S.C. 154(b) by 0 days.

(21) Appl. No.: 19/014,175

(22) Filed: Jan. 8, 2025

(30) Foreign Application Priority Data

Jun. 13, 2024 (CN) .......................... 202410757289.5

(51) Int. Cl.
*G01N 29/14* (2006.01)
*G01N 33/22* (2006.01)

(52) U.S. Cl.
CPC .............. *G01N 29/14* (2013.01); *G01N 33/22* (2013.01)

(58) Field of Classification Search
CPC ................................. G01N 29/14; G01N 33/32
USPC ........................................................ 73/35.15
See application file for complete search history.

(56) References Cited

U.S. PATENT DOCUMENTS

| 5,719,791 | A | * | 2/1998 | Neumeier | F23N 5/16 |
| | | | | | 700/274 |
| 6,054,521 | A | * | 4/2000 | Nelson | F02K 9/346 |
| | | | | | 525/123 |
| 11,480,136 | B1 | * | 10/2022 | Smith | F02K 9/52 |
| 2023/0146763 | A1 | * | 5/2023 | Maher | G01N 29/045 |
| | | | | | 73/579 |

FOREIGN PATENT DOCUMENTS

| CN | 102095800 A | | 6/2011 |
| CN | 113530716 | * | 10/2021 |
| CN | 115656413 A | | 1/2023 |
| CN | 118519157 | * | 8/2024 |
| JP | 2018155546 A | | 10/2018 |

OTHER PUBLICATIONS

Development of an Ultrasonic Burning Rate Measurement Technique, Wu et al., 39th AIAA/ASME/SAE/ASEE Joint Propulsion Conference and Exhibit Jul. 20-23, 2003, Huntsville, Alabama. (Year: 2003).*

* cited by examiner

*Primary Examiner* — Jacques M Saint Surin

(57) ABSTRACT

The present disclosure relates to the technical field of solid engine burning rate test, and provides a method and system for measuring the burning rate of a propellant based on multi-channel ultrasonic waves. The method includes the following steps: collecting echo signals and corresponding noise signals of each ultrasonic channel, and pre-processing same; and finding a period of two adjacent echoes with the maximum amplitude difference, and the maximum peak of an echo period of current frame. In the present disclosure, the accuracy of echo moment is improved, and the burning rate is accurately measured under high noise environment.

9 Claims, 4 Drawing Sheets

METHOD AND SYSTEM FOR MEASURING BURNING RATE OF PROPELLANT BASED ON MULTI-CHANNEL ULTRASONIC WAVES

CROSS-REFERENCE TO RELATED APPLICATION

This application claims priority of Chinese Patent Application No. 202410757289.5, filed on Jun. 13, 2024, the entire contents of which are incorporated herein by reference.

TECHNICAL FIELD

The present disclosure relates to the technical field of solid engine burning rate test, and in particular to a method and system for measuring the burning rate of a propellant based on multi-channel ultrasonic waves.

BACKGROUND

The burning rate of the solid propellant determines the engine thrust of the rocket, and ultimately the flight velocity of the rocket. The change of the influence factors including pressure, initial temperature and burning rate during combustion will eventually be reflected in the change of burning rate, and therefore the burning rate test has very important significance. The test methods for the burning rate of solid propellant can be divided into static test method and dynamic test method. Compared with the static test method, the dynamic test method can reflect the real-time burning state of solid propellant more intuitively. The ultrasonic dynamic burning rate test technology has the characteristics of easy to use, good real-time and high resolution, enabling rapid and accurate acquisition of burning rate data, and realizing the real-time dynamic monitoring of the burning rate, which is of great significance to the adjustment of the rocket flight parameters and the accuracy of the flight trajectory. Therefore, the ultrasonic burning rate test system with non-contact dynamic test characteristics will become the main means of burning rate test in the future.

The ultrasonic burning rate test method is to measure the real-time thickness of propellant by using pulse echo method. In the process of passing through the shell, thermal insulation layer and propellant, sound waves will echo at different interfaces due to different acoustic impedances of different media. By recording the time difference between ultrasonic transmission and reception, the position of burning surface can be calculated according to the known sound velocity of the medium, and the burning rate can be obtained by measuring the position of burning surface at different moments. However, in the actual test of burning rate of solid rocket engine, since the solid rocket engine includes shell, thermal insulation layer and solid propellant, the ultrasonic wave will be attenuated in different degrees in the propagation process, and with the increase of the overall thickness, the echo energy of the burning surface will be greatly reduced. At the same time, due to the engine working in a harsh environment of strong vibration and strong electromagnetic interference, the weak ultrasonic echo signal is often submerged in the background noise. Therefore, it is the key to extract the echo signal and accurately locate the moment when the echo signal appears, which is related to the test accuracy of the whole system.

The existing ultrasonic burning rate measurement system can meet the basic test requirements in the case of small noise interference, but the accurate burning rate data is difficult to obtain in the environment of high noise and small signal. Therefore, it is necessary to improve the existing propellant burning rate measurement method to enhance the accuracy and precision of the burning rate measurement.

SUMMARY

To overcome the problem of low accuracy of propellant burning rate measurement in the prior art, the present disclosure provides a method and system for measuring the burning rate of a propellant based on multi-channel ultrasonic waves to enhance the accuracy and precision of burning rate measurement by improving the accuracy of the moment when a burning surface echo appears.

To solve the above-mentioned technical problems, the technical solutions adopted by the present disclosure are as follows. A method for measuring the burning rate of a propellant based on multi-channel ultrasonic waves includes the following steps:

step 1: opening a noise collection channel and an ultrasonic channel, and transmitting ultrasonic waves to a solid propellant in an engine outer shell via a plurality of ultrasonic transducers arranged on the same circumference of the engine outer shell;

step 2: collecting echo signals and corresponding noise signals of each ultrasonic channel, and pre-processing the echo signals;

step 3: calculating a range of first echo time $t_3$ based on acoustic properties of material being tested;

step 4: acquiring first frame of data, finding two adjacent echoes with the maximum amplitude difference in a current frame, and the maximum wave peak of an echo period of the current frame, and calculating a threshold coefficient;

step 5: traversing a wavelet basis set to screen an optimal wavelet basis, performing wavelet packet decomposition on echo data of the current frame via the screened optimal wavelet basis, performing denoising processing and signal reconstruction on wavelet packet decomposition signals via a standard deviation of the noise signal collected in step 2, and performing time-frequency analysis on reconstructed signals to obtain a time range of a waveform appearing corresponding to an echo frequency as a range of a second echo time $t_n$;

step 6: determining a range of a final echo time $t_x$ according to a range of the first echo time $t_3$ and the second echo time $t_n$;

step 7: performing time difference extraction within the range of the final echo time $t_x$, and determining a dynamic threshold of the current frame according to the threshold coefficient obtained in step 4, and obtaining an echo moment of the current frame according to the dynamic threshold of the current frame;

step 8: acquiring next frame of data, and repeating the above-mentioned steps 5-7 to obtain an echo moment corresponding to each frame of data;

step 9: repeating the above-mentioned steps 3-8 for echo data and noise data of each channel to obtain an echo moment corresponding to each frame of data in each channel; and calculating a burning rate according to the echo moment corresponding to each frame of data in each channel.

In step 4, a calculation formula of the threshold coefficient A is as follows:

$$A = \frac{A_x + A_{x+1}}{2A_{MAX}},$$

where $A_{MAX}$ represents the maximum wave peak value in the echo period of the current frame, and $A_x$ and $A_{x+1}$ respectively represent amplitudes of the two adjacent echoes with the maximum amplitude difference.

In step 3, a range of the first echo time $t_3$ is:

$$\frac{2 \times D_1}{V_{sound1}} + \frac{2 \times D_2}{V_{sound2}} < t_3 < \frac{2 \times D_1}{V_{sound1}} + \frac{2 \times D_2}{V_{sound2}} + \frac{2 \times D_3}{V_{sound3}}$$

where $D_1$, $D_2$, and $D_3$ represent initial thicknesses of materials of an outer shell layer, a thermal insulation layer, and a propellant layer, respectively, and $V_{sound1}$, $V_{sound2}$, and $V_{sound3}$ represent sound propagation velocities in the outer shell layer, the thermal insulation layer, and the propellant layer, respectively.

In step 5, a method for screening the optimal wavelet basis is as follows: traversing a set of wavelet basis functions $\{\omega_1, \omega_2 \ldots \omega_i \ldots, \omega_n\}$, where $\omega_1, \omega_2 \ldots \omega_i \ldots, \omega_n$, represent the $1_{st}$, $2_{nd}$, ... $i_{th}$ ..., and $n_{th}$ wavelet bases respectively, calculating an energy concentration degree factor C corresponding to each wavelet basis function, and selecting a wavelet basis function with a value of the energy concentration degree factor C closest to 1 as the optimal wavelet basis.

In step 5, when performing denoising processing, a fixed multiple of the standard deviation of the noise signal is selected as a wavelet threshold to perform denoising processing on the wavelet packet decomposition signals.

In step 6, a range of the final echo time $t_x$ is $t_x \in t_3 \cap t_n$.

In step 7, the obtaining an echo moment of the current frame includes the following specific steps:

multiplying the threshold coefficient by the maximum echo peak value of the current frame as the dynamic threshold of the current frame, taking a first wave peak before the dynamic threshold as a characteristic wave of the current frame signal, recording a period number m corresponding to the characteristic wave, and seeking a moment corresponding to the $2m_{th}$ zero point forward from the characteristic wave as the echo moment of the current frame.

In step 9, the calculating a burning rate includes the following specific steps:

firstly, calculating the burning rate V of each channel in the corresponding time period, a calculation formula being as follows:

$$V = \frac{\nabla_{sound3} \times |T_N \cdot T_0|}{2 \times N \times T}, N \geq 1,$$

where T represents an emission period of ultrasonic wave, $T_N$ represents an echo moment of the $(N+1)_{th}$ frame of data, N represents a number of frames in a corresponding time period, $T_0$ represents an echo moment of first frame of data, and $V_{sound3}$ represents a sound propagation velocity in the propellant layer; and taking an average burning rate of each channel in the corresponding time period as the burning rate in this time period.

In addition, the present disclosure also provides a system for measuring the burning rate of a propellant based on multi-channel ultrasonic waves used for implementing the method for measuring the burning rate of a propellant based on multi-channel ultrasonic waves, including a plurality of ultrasonic transducers, a transceiving isolation module, a signal processing module, a data storage module and a data processing module;

each of the ultrasonic transducers is arranged at a different position on the same circumference of an engine outer shell;

a signal output end of each of the ultrasonic transducers is connected to the signal processing module via the transceiving isolation module, an output end of the signal processing module is connected to the data storage module, and the data storage module is connected to the data processing module via a peripheral component interconnect express (PCIE) transmission module;

the signal processing module is used for executing step 2;

the data storage module is used for storing echo data and noise data of each channel; and the data processing module is used for executing steps 3-9.

The signal processing module includes an echo gain filtering module and an analog-to-digital conversion module, an output end of the data processing module is connected to a control end of the echo gain filtering module, and the data processing module is further used for adjusting the gain size of the echo gain filtering module according to an echo peak value to obtain the maximum echo peak value.

The present disclosure has the following advantageous effects compared with the prior art.

The present disclosure provides a method and system for measuring the burning rate of a propellant based on multi-channel ultrasonic waves. The collected data are transmitted to the data processing module through independent noise collection channel and echo collection channel, and the data processing module acquires and synchronously suppresses noise information. At the same time, the echo signal is fed back to the echo gain filtering module in real-time to adjust the echo gain to obtain the optimal signal to noise ratio. In signal processing, the echo signal is traversed by the wavelet basis function, and the optimal wavelet basis is selected according to the wavelet energy concentration factor for wavelet packet decomposition. The echo time range is optimized by the above-mentioned adaptive wavelet basis echo signal extraction and noise active suppression algorithm, and the interference of the noise signal on the echo extraction is minimized. The echo time range is further optimized by the acoustic properties of materials. Finally, the echo moment is accurately located by the time difference extraction algorithm, which improves the solution accuracy and efficiency of the echo moment. The displacement of the burning surface and the burning rate in each time period can be calculated from the echo moment of each frame, achieving the accurate measurement of burning rate in high noise environment. In addition, the measurement system of the present disclosure uses multi-channel parallel sampling at the same time, the sampled data located at the same circumference are similar, and finally, the complementary correction of the results of each channel can further improve the effectiveness and accuracy of the test results. Therefore, the present disclosure improves the test system, optimizes the data processing algorithm, and improves the accuracy of the calculation of the burning rate.

DETAILED DESCRIPTION

To explain the objectives, technical solutions and advantages of examples of the present disclosure more clearly, the technical solutions in the examples of the present disclosure will be described clearly and completely in the following. Obviously, all the described examples are only some, rather than all examples of the present disclosure. On the basis of the examples in the present disclosure, all other examples obtained by those ordinary skilled in the art without creative efforts belong to the protection scope of the present disclosure.

Example 1

Figure 1:
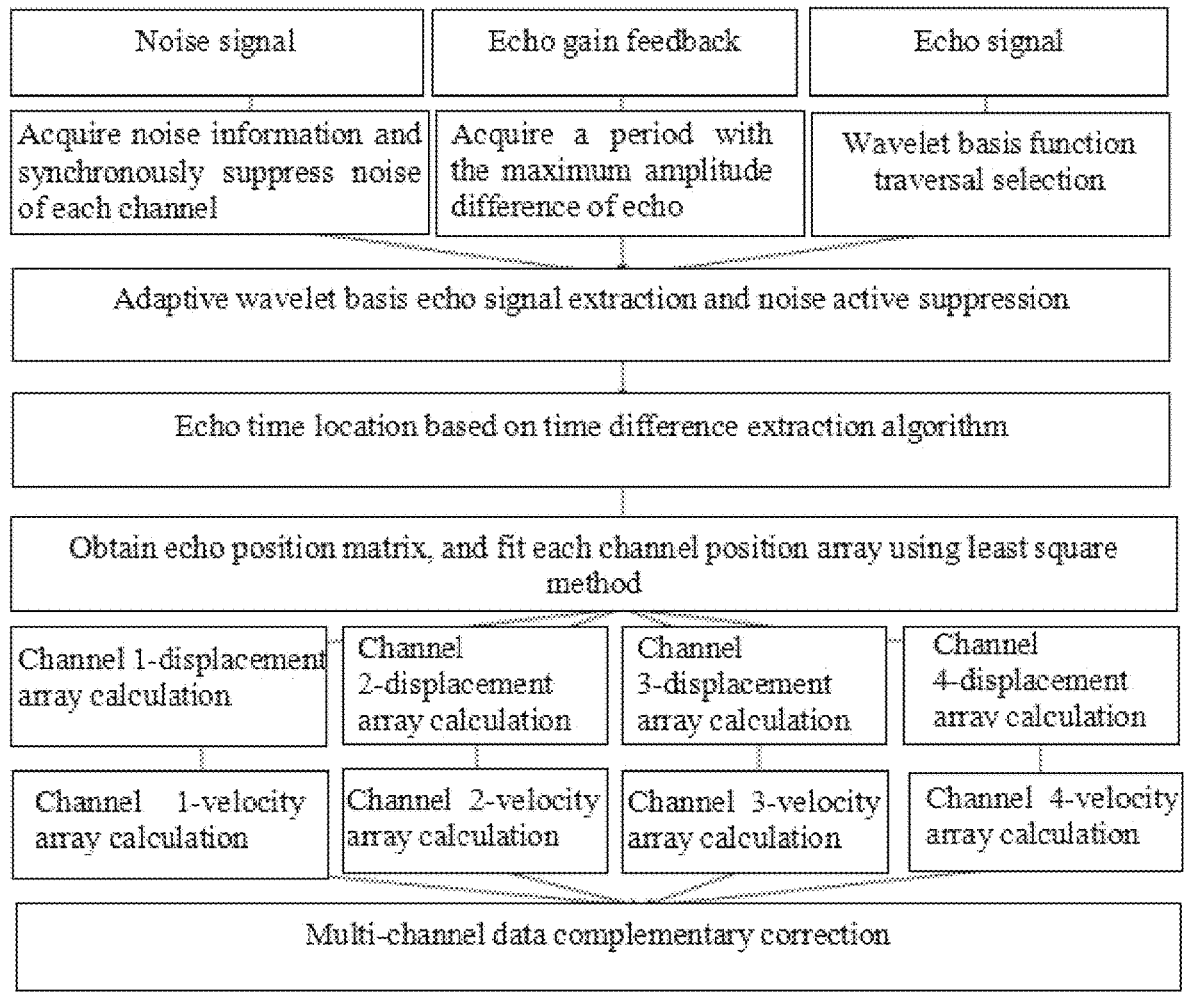
FIG. 1 is a schematic diagram of principle of a method for measuring the burning rate of a propellant based on multi-channel ultrasonic waves according to Example 1 of the present disclosure.
Figure 2:
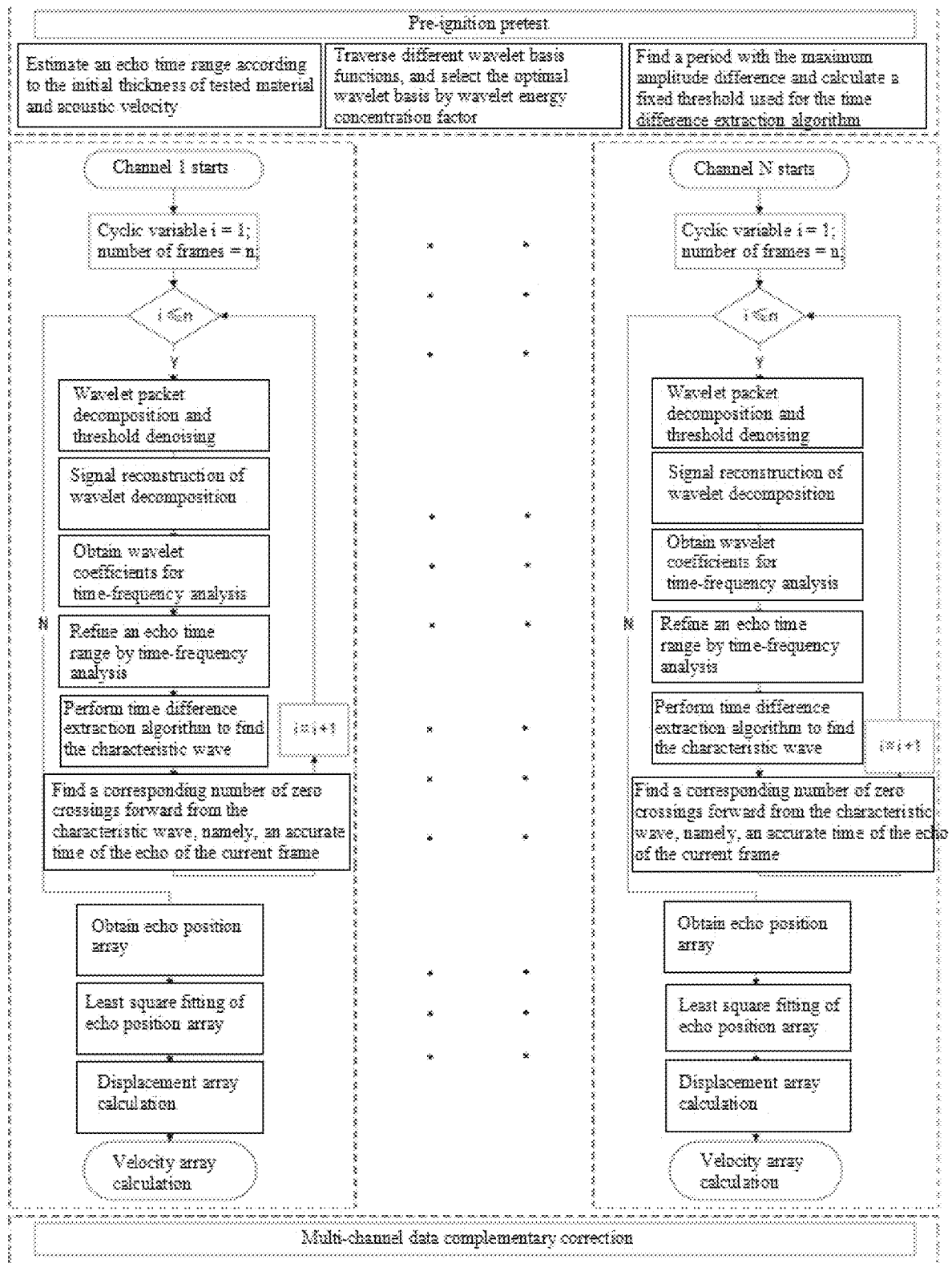
FIG. 2 is a flow diagram of the method for measuring the burning rate of a propellant based on multi-channel ultrasonic waves according to Example 1 of the present disclosure.

As shown in FIGS. 1-2, an example of the present disclosure provides a method for measuring the burning rate of a propellant based on multi-channel ultrasonic waves, including the following steps:

Step 1, a noise collection channel and an ultrasonic channel are opened, and ultrasonic waves are transmitted to a solid propellant in an engine outer shell via a plurality of ultrasonic transducers arranged on the same circumference of the engine outer shell.

Step 2, echo signals and corresponding noise signals of each ultrasonic channel are collected, and the echo signals are pre-processed.

When the engine is not ignited, ultrasonic waves are transmitted at the farthest distance and attenuated to the greatest extent, and ultrasonic excitation pulse parameters need to be set when the engine is not ignited before the signal is collected.

Specifically, in this example, the echo signal from the ultrasonic transducer of each channel is received by a transceiving isolation module, each echo signal is filtered and amplified by a gain filtering module, and each echo signal is subjected to analog-to-digital conversion by an analog-to-digital conversion module. In addition, to obtain a larger echo signal, the signal pre-processing process further includes step of adjusting the gain size of the gain filtering module by an echo signal peak value.

Step 3, a range of the first echo time $t_3$ is calculated on the basis of the acoustic properties of material being tested.

The tested engine structure is generally stacked with three layers of materials, including an outer shell layer, a thermal insulation layer, and a propellant layer; and it is known that initial thicknesses of the materials of the respective layers are $D_1$, $D_2$, and $D_3$ respectively. In the dynamic test process, the thicknesses of the outer shell layer and the thermal insulation layer are constant, and the thickness of the propellant layer varies over time. Assuming that a sound propagation velocity in the outer shell is $V_{sound1}$, a sound propagation velocity in the thermal insulation layer is $V_{sound2}$, and a sound propagation velocity in the propellant layer is $V_{sound3}$, according to the formula of pulse echo method, a time $t_1$ when the echo appears at an interface between the outer shell and the thermal insulation layer is calculated as:

$$t_1 = \frac{2 \times D_1}{V_{sound1}}. \tag{1}$$

A time when the echo appearing at an interface of the thermal insulation layer and the propellant layer appears is:

$$t_2 = \frac{2 \times D_1}{V_{sound1}} + \frac{2 \times D_2}{V_{sound2}}. \tag{2}$$

A time range of the echo appearing at the interface between the propellant layer and an air layer is taken as the first echo time $t_3$ range, and a calculation formula thereof is:

$$\frac{2 \times D_1}{V_{sound1}} + \frac{2 \times D_2}{V_{sound2}} < t_3 < \frac{2 \times D_1}{V_{sound1}} + \frac{2 \times D_2}{V_{sound2}} + \frac{2 \times D_3}{V_{sound3}}. \tag{3}$$

The thickness of outer shell layer and thermal insulation layer remains unchanged, and an initial thickness of propellant layer is $D_3$, which gradually decreases over time until the thickness becomes 0. Therefore, the time range of echo appearing at the interface between the propellant layer and the air layer is calculated first, which can reduce a range for solving echo moment and improve the speed and accuracy of data processing.

Step 4, two adjacent echoes with the maximum amplitude difference in the current frame and the maximum wave peak of echo period of the current frame are found, and a threshold coefficient is calculated.

Amplitude coefficients of the two adjacent echoes with the maximum amplitude difference are as follows:

$$C_x = \frac{A_x}{A_{MAX}}, \; C_{x+1} = \frac{A_{x+1}}{A_{MAX}}, \tag{4}$$

where $C_x$ and $C_{x+1}$ represent the amplitude coefficients of the two adjacent echoes with the maximum amplitude difference, $A_{MAX}$ represents the maximum wave peak value in the echo period of the current frame, and $A_x$ and $A_{x+1}$ represent amplitudes of the two adjacent echoes with the maximum amplitude difference. x and x+1 represent periods where the two adjacent echoes with the maximum amplitude difference are located. In this example, an average value $$\frac{C_x + C_{x+1}}{2}$$

of the amplitude coefficients of the two adjacent echoes with the maximum amplitude difference is taken as a threshold coefficient of time difference extraction algorithm, which can ensure that the threshold point is after the x peak and before the x+1 peak. In step 3, a calculation formula of the threshold coefficient A is:

$$A = \frac{C_x + C_{x+1}}{2} = \frac{A_x + A_{x+1}}{2A_{MAX}}. \quad (5)$$

Step 5: the optimal wavelet base is screened by traversing a wavelet basis set, the wavelet packet decomposition is performed on echo data of the current frame to obtain an approximation coefficient $C_A$ and a detail coefficient $C_D$ through the optimal wavelet basis obtained by screening, wavelet threshold denoising is performed on the wavelet packet decomposition coefficient by the standard deviation of the noise signal collected in step 2, the wavelet packet decomposition coefficients of the noise part less than the threshold are set to zero or compressed, and finally the wavelet packet decomposition coefficients after the wavelet threshold denoising processing are reconstructed. Through the approximation coefficient $C_A$ and the detail coefficient $C_D$, the time-frequency analysis of the reconstructed signal is performed, and a time range in which the waveform appears corresponding to the echo frequency is obtained as a range of the second echo time to of the current frame.

The approximation coefficient $C_A$ represents a low-frequency part of the signal and the detail coefficient $C_D$ represents a high-frequency part of the signal, and these coefficients reflect the characteristics of the signal at different frequencies and scales. The coefficients of wavelet packet decomposition are needed for the time-frequency analysis and wavelet threshold denoising based on wavelet packet transform. In addition, the standard deviation of the noise signal measures the strength of the noise signal, and can be used to help determine the threshold in wavelet threshold denoising. Wavelet threshold denoising processing is performed on the wavelet packet decomposition coefficients, the wavelet packet decomposition coefficients of the noise part less than the threshold are set to zero or compressed, and the processed wavelet packet decomposition coefficients are reconstructed to obtain a denoised signal. The wavelet packet decomposition coefficients include the approximation coefficient $C_A$ and the detail coefficient $C_D$, which reflect the frequency and scale information of the signal at different frequencies, and the reconstructed signal after denoising can be analyzed in time domain and frequency domain at the same time. With the known above-mentioned frequency of the echo signal, during the time-frequency analysis, the moment when a frequency is equal to a frequency of the echo signal appearing can be found.

In step 5, a method for screening the optimal wavelet basis is as follows: traversing a set of wavelet basis functions $\{\omega_1, \omega_2 \ldots \omega_i \ldots, \omega_n\}$, where $\omega_1, \omega_2 \ldots \omega_i \ldots \omega_n$, represent the $1_{st}, 2_{nd}, \ldots i_{th} \ldots$, and $n_{th}$ wavelet bases respectively, an energy concentration degree factor C corresponding to each wavelet basis function is calculated with the following calculation formula:

$$C = \frac{(MAX/\omega[n]^2/)}{\sum /\omega[n]^2/}, \quad (6)$$

where $MAX/\omega[n]^2/$ represents a square of the maximum amplitude of the $n_{th}$ wavelet basis, and E represents a total energy of the wavelet basis.

In this example, the wavelet basis function with a value of the energy concentration factor C closest to 1 is selected as the optimal wavelet basis. Since each frame of data has a high degree of similarity, and only the echo appears at a different time, in this example, it is only necessary to traverse the wavelet basis set to screen the optimal wavelet basis during processing the first frame of data, and the wavelet processing process of all frames can be analyzed according to the optimal wavelet basis selected from the first frame.

In step 5, when performing denoising processing, a fixed multiple of the standard deviation of the noise signal is selected as a wavelet threshold to perform denoising processing on the wavelet packet decomposition signals.

Step 6, according to ranges of the first echo time $t_3$ and the second echo time $t_n$, a range of a final echo time $t_x$ is determined.

In step 6, the range of the final echo time $t_x$ is $t_x \in t_3 \cap t_n$. By determining the range of the final echo time $t_x$ as a time range of time difference extraction, a time range of echo appearing can be reduced, and the accuracy and efficiency of the calculation can be improved.

Step 7: time difference extraction is performed within the range of the final echo time, and a dynamic threshold of the current frame is determined according to the threshold coefficient obtained in step 4, and an echo moment of the current frame is obtained according to the dynamic threshold of the current frame.

In step 7, the specific method for extracting the time difference within the range of the final echo time to obtain the echo moment of the current frame is as follows. The threshold coefficient is multiplied by the maximum echo peak value of the current frame as the dynamic threshold of the current frame, and the first peak before the dynamic threshold is taken as a characteristic wave of the current frame of signal. A period number m corresponding to the characteristic wave is recorded, and a moment corresponding to the $2m_{th}$ zero point is found forward from the characteristic wave and is taken as the echo moment of the current frame.

Since the echo signals tested by the ultrasonic transducer have a high correlation, a period with the maximum amplitude difference of each echo is at the same position. Therefore, the threshold coefficient A is multiplied by the maximum echo peak of the current frame to obtain a result as the dynamic threshold of the current frame. The echo moment of the current frame can be determined, and the velocity for searching for the echo moment can be improved.

Specifically, a determination method for the first peak before the dynamic threshold is as follows. With the dynamic threshold as the ordinate, a horizontal baseline parallel to a horizontal axis is drawn. A peak is searched for along a negative direction of the horizontal axis from an intersection point between the baseline and the echo signal, and the first peak found is the first peak before the dynamic threshold.

Figure 3:
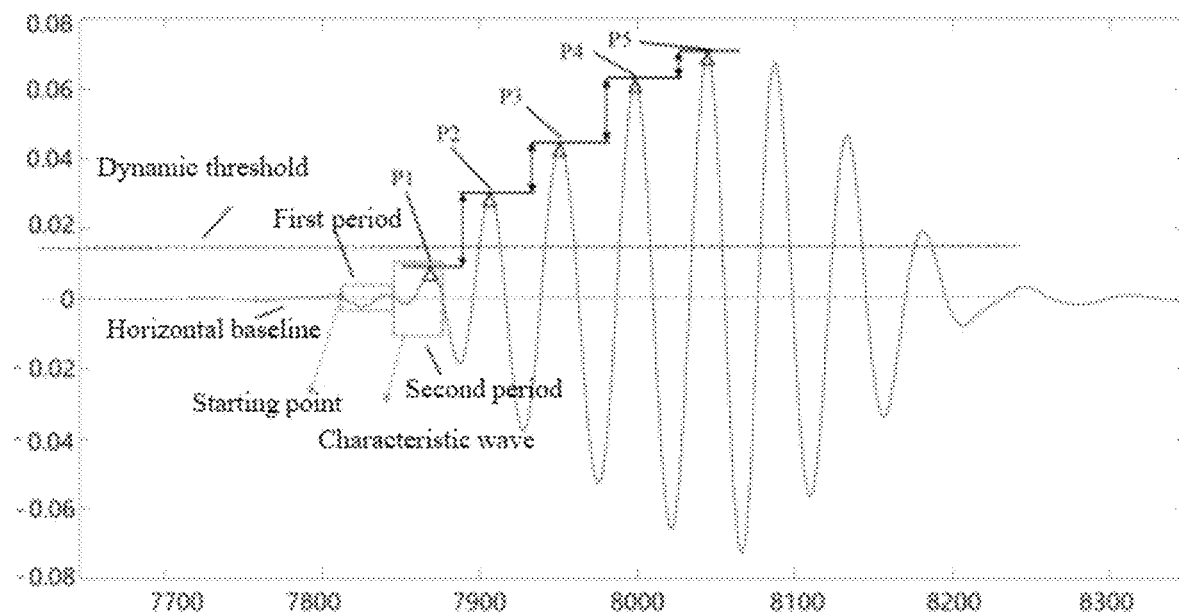
FIG. 3 is a schematic diagram of the first frame of echo signal obtained in Example 1 of the present disclosure.

FIG. 3 shows the first frame of echo signal measured by the ultrasonic transducer. The specific method for finding the echo moment is described by taking this signal as an example. Firstly, a peak P5 with the maximum peak in the echo is found, and the peak difference between adjacent peaks before the peak P5 is calculated, with the peak difference between the peak P1 and the peak P2 being maximum. Since the echo signals measured at each time are very similar, the echo signals of other frames also have the maximum peak difference at the same position. In order to automatically find a position where the peak difference is maximum each time, a threshold coefficient is set in this example. When the maximum peak of the echo signal of the frame is multiplied by the threshold coefficient, a certain height position between two peaks with the maximum peak difference is automatically located; and a straight line drawn with the height serves as the dynamic threshold. A characteristic peak can be found forward from the intersection point between the dynamic threshold and the echo signal, and the echo moment of the current frame can be quickly determined according to the characteristic peak.

The threshold coefficient A=0.2686 can be obtained by calculating the echo data in FIG. 3 using formula (5), and the dynamic threshold for the frame signal is 0.2686× 0.0698=0.0187. The first peak P1 before the dynamic threshold is taken as a characteristic wave of the current frame signal, and a period number m of the echo corresponding to the peak P1 is recorded. It can be seen in FIG. 3 that the peak P1 is in the second period, i.e. m=2. 2m zero-crossings are found before the characteristic wavefront as a starting point of the echo of the current frame, that is, 4 zero-crossings found forward from the horizontal baseline are the starting point of the echo, and the position is $7811_{th}$ point.

Figure 4:
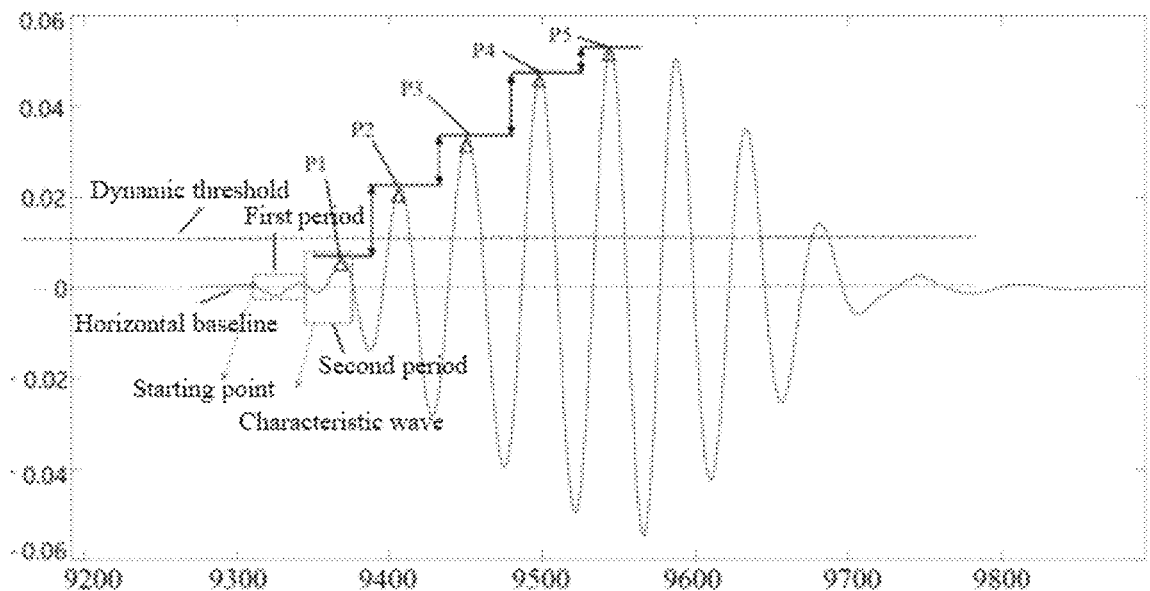
FIG. 4 is a schematic diagram of another frame of echo signal obtained in Example 1 of the present disclosure.

FIG. 4 shows another frame of signal measured by the ultrasonic transducer. Since the same ultrasonic transducer is used, the frame signals are similar. Therefore, the threshold coefficient remains unchanged, and only the dynamic threshold changes. In this case, the dynamic threshold is 0.2686× 0.05235=0.0141. FIG. 4 demonstrates that for different frame signals of the same ultrasound transducer, the dynamic threshold lies between the two peaks with the maximum difference in amplitude. Therefore, in this example of the present disclosure, the echo starting point of this frame signal can be obtained through the dynamic threshold, and the position is $9312_{th}$ point. After the echo starting point is determined, the echo moment of the current frame can be determined according to the extracted time difference value. Taking an analog-to-digital converter (ADC) sampling rate of 20 M as an example, each sampling period is 1/20 M, that is, 50 ns, the relative echo moment corresponding to the $9312_{th}$ point is 9312×50 ns=465.6 us. Combined with the extracted time difference value, the absolute echo time can be obtained.

Step 8: the above-mentioned steps 5-7 are repeated for each frame of data to obtain an echo moment corresponding to each frame of data.

Further, in this example, through the above-mentioned steps 5-7, an echo moment can be obtained for each frame of echo signals. A least square fitting is performed on an array including each echo moment to obtain a relationship curve between the frame and the echo moment, and the echo moment corresponding to each frame is corrected according to the fitted curve, further eliminating a point position at which the zero-crossing point caused by noise interference is inaccurate and leads to inaccurate determination of the echo moment of a certain frame.

Step 9: the above-mentioned steps 3-8 for echo data and noise data of each channel are repeated to obtain an echo moment corresponding to each frame of data in each channel; and the burning rate is calculated according to the echo moment corresponding to each frame of data in each channel.

Assuming that the echo moment corresponding to the $i_{th}$ frame is $T_i$(i=1, 2, 3 . . . , n), and n is the number of frames. $T_i$ minus the time $t_1$ and $t_2$ for ultrasonic wave to pass through the outer shell and thermal insulation layer to obtain a transit time for the ultrasonic wave to pass through the propellant thickness. Therefore, the propellant thickness D in the frame period can be calculated as:

$$D = \frac{V_{sound3} \times (T_i - t_1 - t_2)}{2}. \qquad (7)$$

According to formula (7), the corresponding propellant thickness of each frame of data can be calculated, and according to the difference between the thicknesses of two adjacent frames and the time difference (equal to an emission period of the ultrasonic wave), the burning rate corresponding to each frame of data can be calculated.

In addition, this example can calculate the burning rate in each time period. The specific methods are as follows.

(1) The burning rate V of each channel in corresponding time period is calculated, and a calculation formula is as follows:

$$V = \frac{V_{sound3} \times |T_N - T_0|}{2 \times N \times T}, N \geq 1, \qquad (8)$$

where T represents emission periods of ultrasonic waves, N represents a number of frames in a corresponding time period, $T_N$ represents an echo moment of the $(N+1)_{th}$ frame of data, $T_0$ represents an echo moment of the first frame of data, and $V_{sound3}$ represents a sound propagation velocity in the propellant layer.

(2) An average burning rate of each channel in the corresponding time period is taken as the burning rate in this time period, and the accuracy of the burning rate measurement can be improved.

Example 2

Figure 5:
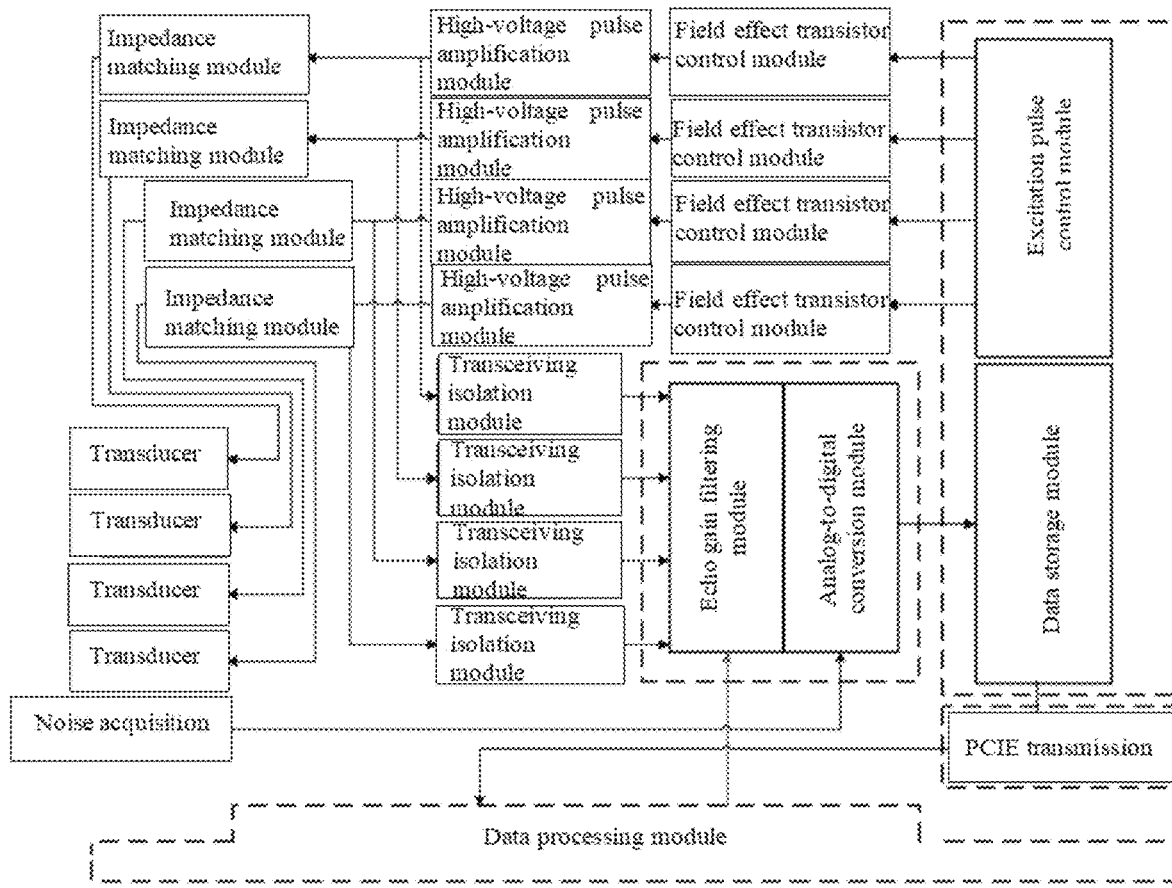
FIG. 5 is a block diagram showing the structure of a device for measuring the burning rate of a propellant based on multi-channel ultrasonic waves according to Example 2 of the present disclosure.

As shown in FIG. 5, Example 2 of the present disclosure provides a system for measuring the burning rate of a propellant based on multi-channel ultrasonic waves, including a plurality of ultrasonic transducers, a transceiving isolation module, a signal processing module, a data storage module and a data processing module. Each of the ultrasonic transducers is arranged at a different position on the same circumference of the engine outer shell; and a signal output end of each of the ultrasonic transducers is connected to the signal processing module via the transceiving isolation module, an output end of the signal processing module is connected to the data storage module, and the data storage module is connected to the data processing module via a PCIE transmission module.

Specifically, the signal processing module executes step 2 in Example 1, namely, the signal processing module is used for collecting echo signals and corresponding noise signals of each of the ultrasonic channels, and pre-processing the echo signals; the data storage module is used for storing echo data and noise data of each channel; and the data processing module is used for executing steps 3-9 in Example 1, namely, the burning rate in each time period is calculated according to the echo signals of each channel.

Further, as shown in FIG. 5, in this example, the signal processing module includes an echo gain filtering module and an analog-to-digital conversion module, an output end of the data processing module is connected to a control end of the echo gain filtering module, and the data processing module is further used for adjusting the gain size of the echo gain filtering module according to an echo peak value to adjust the signal-to-noise ratio of the echo signal.

Further, the measurement system in this example further includes a noise acquisition module and an excitation module. The excitation module is used for driving the ultrasonic transducers, and specifically includes an excitation pulse control module, a field effect transistor control module, a high-voltage pulse amplification module and an impedance matching block. A pulse signal sent by the excitation pulse control module is sent to the ultrasonic transducers after passing through the field effect transistor control module, the high-voltage pulse amplification module and the impedance matching module in sequence, driving same to send out ultrasonic signals. After passing through an engine outer shell, a thermal insulation layer and a propellant, the ultrasonic wave is reflected at a propellant combustion interface, and the reflected echo signal is received by the ultrasonic transducers after passing through the propellant and the engine outer shell in sequence. After being received by the ultrasonic transducers, the echo signal is isolated from the high-voltage signal by the transceiving isolation module, and is pre-processed by the echo gain filtering module and the analogue-to-digital conversion module; and the obtained digital signal is stored in the data storage module, and is sent to the data processing module by the PCIE transmission module for propellant burning rate calculation.

The present disclosure provides a method and system for measuring the burning rate of a propellant based on multi-channel ultrasonic waves, the collected data are transmitted to the data processing module through independent noise collection channel and echo collection channel, and the data processing module acquires and synchronously suppresses noise information. At the same time, the echo signal is fed back to the echo gain filtering module in real-time to adjust the echo gain to obtain the optimal signal to noise ratio. In signal processing, the echo signal is traversed by the wavelet basis function, and an optimal wavelet basis is selected according to a wavelet energy concentration factor for wavelet packet decomposition. An echo time range is optimized by the above-mentioned adaptive wavelet basis echo signal extraction and noise active suppression algorithm, and the echo time range is further optimized by the acoustic properties of materials. Finally, an echo moment is accurately located by time difference extraction algorithm, which improves the solution accuracy and efficiency of the echo moment. The displacement of the burning surface and the burning rate in each period can be calculated from the echo moment of each frame. In addition, the measurement system of the present disclosure uses multi-channel parallel sampling at the same time, the sampled data located at the same circumference are similar, and finally, the complementary correction of the results of each channel can further improve the effectiveness and accuracy of the test results.

Finally, it is to be noted that the above examples are only used to describe technical solutions of the present disclosure, and are not to limit the present disclosure. Although the present disclosure has been described in detail with reference to the foregoing examples, those skilled in the art will understand that the technical solutions disclosed in the above examples can still be modified, or some of the technical features thereof can be replaced by equivalents. However, these modifications and replacements do not make the essence of the corresponding technical solutions depart from the spirit and scope of the technical solutions of various examples of the present disclosure.

The invention claimed is:

1. A method for measuring the burning rate of a propellant based on multi-channel ultrasonic waves, comprising the following steps:
   step 1: opening a noise collection channel and an ultrasonic channel, and transmitting ultrasonic waves to a solid propellant in an engine outer shell via a plurality of ultrasonic transducers arranged on the same circumference of the engine outer shell;
   step 2: collecting echo signals and corresponding noise signals of each ultrasonic channel, and pre-processing the echo signals;
   step 3: calculating a range of first echo time $t_3$ based on acoustic properties of material being tested;
   step 4: acquiring first frame of data, finding two adjacent echoes with the maximum amplitude difference in a current frame and the maximum wave peak of an echo period of the current frame, and calculating a threshold coefficient; a calculation formula of the threshold coefficient A in step 4 being as follows:

$$A = \frac{A_x + A_{x+1}}{2A_{MAX}},$$

where $A_{MAX}$ represents the maximum wave peak value in the echo period of the current frame, and $A_x$ and $A_{x+1}$ respectively represent amplitudes of the two adjacent echoes with the maximum amplitude difference;
   step 5: traversing a wavelet basis set to screen an optimal wavelet basis, performing wavelet packet decomposition on echo data of the current frame via the screened optimal wavelet basis, performing denoising processing and signal reconstruction on wavelet packet decomposition signals via a standard deviation of the noise signal collected in step 2, and performing time-frequency analysis on reconstructed signals to obtain a time range of a waveform appearing corresponding to an echo frequency as a range of a second echo time $t_n$; in step 5, a method for screening the optimal wavelet basis being as follows: traversing a set of wavelet basis functions $\{\omega_1, \omega_2 \ldots \omega_i \ldots, \omega_n\}$, where $\omega_1, \omega_2 \ldots \omega_i \ldots \omega_n$, represent the $1_{st}, 2_{nd}, \ldots i_{th} \ldots$, and $n_{th}$ wavelet bases respectively, calculating an energy concentration degree factor C corresponding to each wavelet basis function, and selecting a wavelet basis function with a value of the energy concentration degree factor C closest to 1 as the optimal wavelet basis, a calculation formula being as follows:

$$C = \frac{(MAX/\omega[n]^2/)}{E},$$

where $MAX/\omega[n]^2/$ represents a square of the maximum amplitude of the $n_{th}$ wavelet basis, and E represents a total energy of the wavelet basis; and
   in step 5, when performing denoising processing, a fixed multiple of the standard deviation of the noise signal being selected as a wavelet threshold to perform denoising processing on the wavelet packet decomposition signals;
   step 6: determining a range of a final echo time $t_x$ according to ranges of the first echo time $t_3$ and the second echo time $t_n$, a range of the final echo time $t_x$ being $t_x \in t_3 \cap t_n$;

step 7: performing time difference extraction within the range of the final echo time $t_x$, and determining a dynamic threshold of the current frame according to the threshold coefficient obtained in step 4, and obtaining an echo moment of the current frame according to the dynamic threshold of the current frame;

step 8: acquiring next frame of data, and repeating the above-mentioned steps 5-7 to obtain an echo moment corresponding to each frame of data; and step 9: repeating the above-mentioned steps 3-8 for echo data and noise data of each channel to obtain an echo moment corresponding to each frame of data in each channel; and calculating a burning rate according to the echo moment corresponding to each frame of data in each channel.

2. The method for measuring the burning rate of a propellant based on multi-channel ultrasonic waves according to claim 1, wherein in step 3, the range of the first echo time $t_3$ is:

$$\frac{2 \times D_1}{V_{sound1}} + \frac{2 \times D_2}{V_{sound2}} < t_3 < \frac{2 \times D_1}{V_{sound1}} + \frac{2 \times D_2}{V_{sound2}} + \frac{2 \times D_3}{V_{sound3}}$$

where $D_1$, $D_2$, and $D_3$ represent initial thicknesses of materials of an outer shell layer, a thermal insulation layer, and a propellant layer, respectively, and $V_{sound1}$, $V_{sound2}$, and $V_{sound3}$ represent sound propagation velocities in the outer shell layer, the thermal insulation layer, and the propellant layer, respectively.

3. The method for measuring the burning rate of a propellant based on multi-channel ultrasonic waves according to claim 1, wherein in step 7, the obtaining an echo moment of the current frame comprises the following specific steps:

multiplying the threshold coefficient by the maximum echo peak value of the current frame as the dynamic threshold of the current frame, taking a first wave peak before the dynamic threshold as a characteristic wave of the current frame signal, recording a period number m corresponding to the characteristic wave, and seeking a moment corresponding to the $2m_{th}$ zero point forward from the characteristic wave as the echo moment of the current frame.

4. The method for measuring the burning rate of a propellant based on multi-channel ultrasonic waves according to claim 1, wherein in step 9, the calculating a burning rate comprises the following specific steps:

firstly, calculating the burning rate V of each channel in the corresponding time period, a calculation formula being as follows:

$$V = \frac{V_{sound3} \times |T_N - T_0|}{2 \times N \times T}, N \geq 1,$$

where T represents an emission period of ultrasonic wave, $T_N$ represents an echo moment of the $(N+1)_{th}$ frame of data, N represents a number of frames in a corresponding time period, $T_0$ represents an echo moment of first frame of data, and $V_{sound3}$ represents a sound propagation velocity in the propellant layer; and taking an average burning rate of each channel in the corresponding time period as the burning rate in this time period.

5. A system for measuring the burning rate of a propellant based on multi-channel ultrasonic waves, used for implementing the method for measuring the burning rate of a propellant based on multi-channel ultrasonic waves according to claim 1, comprising a plurality of ultrasonic transducers, a transceiving isolation module, a signal processing module, a data storage module and a data processing module, wherein each of the ultrasonic transducers is arranged at a different position on the same circumference of an engine outer shell;

a signal output end of each of the ultrasonic transducers is connected to the signal processing module via the transceiving isolation module, an output end of the signal processing module is connected to the data storage module, and the data storage module is connected to the data processing module via a peripheral component interconnect express (PCIE) transmission module;

the signal processing module is used for executing step 2;

the data storage module is used for storing echo data and noise data of each channel; and the data processing module is used for executing steps 3-9.

6. A system for measuring the burning rate of a propellant based on multi-channel ultrasonic waves, used for implementing the method for measuring the burning rate of a propellant based on multi-channel ultrasonic waves according to claim 2, comprising a plurality of ultrasonic transducers, a transceiving isolation module, a signal processing module, a data storage module and a data processing module, wherein each of the ultrasonic transducers is arranged at a different position on the same circumference of an engine outer shell;

a signal output end of each of the ultrasonic transducers is connected to the signal processing module via the transceiving isolation module, an output end of the signal processing module is connected to the data storage module, and the data storage module is connected to the data processing module via a peripheral component interconnect express (PCIE) transmission module;

the signal processing module is used for executing step 2;

the data storage module is used for storing echo data and noise data of each channel; and the data processing module is used for executing steps 3-9.

7. A system for measuring the burning rate of a propellant based on multi-channel ultrasonic waves, used for implementing the method for measuring the burning rate of a propellant based on multi-channel ultrasonic waves according to claim 3, comprising a plurality of ultrasonic transducers, a transceiving isolation module, a signal processing module, a data storage module and a data processing module, wherein each of the ultrasonic transducers is arranged at a different position on the same circumference of an engine outer shell;

a signal output end of each of the ultrasonic transducers is connected to the signal processing module via the transceiving isolation module, an output end of the signal processing module is connected to the data storage module, and the data storage module is connected to the data processing module via a peripheral component interconnect express (PCIE) transmission module;

the signal processing module is used for executing step 2;

the data storage module is used for storing echo data and noise data of each channel; and the data processing module is used for executing steps 3-9.

8. A system for measuring the burning rate of a propellant based on multi-channel ultrasonic waves, used for implementing the method for measuring the burning rate of a propellant based on multi-channel ultrasonic waves according to claim 4, comprising a plurality of ultrasonic transducers, a transceiving isolation module, a signal processing module, a data storage module and a data processing module, wherein each of the ultrasonic transducers is arranged at a different position on the same circumference of an engine outer shell;

a signal output end of each of the ultrasonic transducers is connected to the signal processing module via the transceiving isolation module, an output end of the signal processing module is connected to the data storage module, and the data storage module is connected to the data processing module via a peripheral component interconnect express (PCIE) transmission module;

the signal processing module is used for executing step 2;

the data storage module is used for storing echo data and noise data of each channel; and the data processing module is used for executing steps 3-9.

9. The system for measuring the burning rate of a propellant based on multi-channel ultrasonic waves according to claim 5, wherein the signal processing module comprises an echo gain filtering module and an analog-to-digital conversion module, an output end of the data processing module is connected to a control end of the echo gain filtering module, and the data processing module is further used for adjusting the gain size of the echo gain filtering module according to an echo peak value to obtain the maximum echo peak value.

* * * * *